US005789633A

United States Patent [19]
Beug-Deeb et al.

[11] Patent Number: 5,789,633
[45] Date of Patent: Aug. 4, 1998

[54] AZEOTROPIC OR AZEOTROPE-LIKE COMPOSITIONS OF HYDROFLUORIC ACID WITH DIHALOETHANES

[75] Inventors: Maria U. D. Beug-Deeb, Hockessin, Del.; Barry Asher Mahler, Glen Mills, Pa.; Ralph Newton Miller, Newark, Del.

[73] Assignee: E. I. du Pont de Nemours and Company, Wilmington, Del.

[21] Appl. No.: 617,457

[22] Filed: Mar. 18, 1996

Related U.S. Application Data

[63] Continuation of Ser. No. 468,099, Jun. 6, 1995.

[51] Int. Cl.$^6$ ........................................ C07C 19/00
[52] U.S. Cl. ..................... 570/181; 570/178; 570/262
[58] Field of Search .................... 570/165, 166, 570/167, 168, 169, 134, 181, 178, 262

[56] References Cited

U.S. PATENT DOCUMENTS

| | | | |
|---|---|---|---|
| 2,495,407 | 1/1950 | Chapman et al. | 260/653 |
| 3,190,930 | 6/1965 | Brock et al. | 260/653.6 |
| 3,862,995 | 1/1975 | Martens et al. | 200/653.6 |
| 4,147,733 | 4/1979 | Fiske et al. | 260/653.4 |
| 4,766,258 | 8/1988 | Komatsu et al. | 570/168 |
| 5,008,474 | 4/1991 | Wairseveas et al. | 570/168 |
| 5,155,082 | 10/1992 | Tung et al. | 502/228 |
| 5,208,395 | 5/1993 | Elsheikh | 570/166 |
| 5,396,001 | 3/1995 | Peanstreau | 870/179 |

FOREIGN PATENT DOCUMENTS

| | | |
|---|---|---|
| A 648783 | 12/1964 | Belgium . |
| 715612 | 8/1965 | Canada ............................ 570/165 |
| 832502 | 1/1970 | Canada . |
| 1069019a | 2/1993 | China . |
| 0 187 643 | 4/1989 | European Pat. Off. . |
| 637 579 A1 | 4/1993 | European Pat. Off. . |
| 0 547 930 A1 | 6/1993 | European Pat. Off. . |
| 0 606 482 A1 | 7/1994 | European Pat. Off. . |
| 0 637 579 al | 2/1995 | European Pat. Off. . |
| 0 676 386 A1 | 10/1995 | European Pat. Off. . |
| 0 693 469 A1 | 1/1996 | European Pat. Off. . |
| 48-16487 | 5/1973 | Japan . |
| 53-116304 | 10/1978 | Japan . |
| 341788 | 6/1972 | U.S.S.R. . |
| 423789 | 4/1974 | U.S.S.R. . |
| 466202 | 4/1975 | U.S.S.R. . |
| WO 94/22796 | 10/1994 | WIPO . |
| WO94/22796 | 10/1994 | WIPO . |
| WO94/22797 | 10/1994 | WIPO . |
| WO94/23813 | 10/1994 | WIPO . |

OTHER PUBLICATIONS

Soviet Inventions Illustrated, 183599, Feb. 1965.

*Primary Examiner*—Alan Siegel
*Attorney, Agent, or Firm*—James E. Shipley

[57] ABSTRACT

The instant invention relates to azeotropic or azeotrope-like compositions of hydrofluoric acid with at least one of 1,1-dichloroethane, 1-chloro-1-fluoroethane and 1,1-difluoroethane. The invention also relates to manufacturing processes for separating hydrofluoric acid from a mixture comprising hydrofluoric acid and one or more of the 1,1-dihaloethane.

1 Claim, 6 Drawing Sheets

AZEOTROPIC OR AZEOTROPE-LIKE COMPOSITIONS OF HYDROFLUORIC ACID WITH DIHALOETHANES

This is a continuation of application Ser. No. 08/468,099, filed Jun. 6, 1995.

FIELD OF THE INVENTION

The instant invention relates to azeotropic or azeotrope-like compositions of hydrofluoric acid with at least one of 1,1-dichloroethane, 1-chloro-1-fluoroethane and 1,1-difluoroethane. The invention also relates to processes for separating hydrofluoric acid from a mixture comprising hydrofluoric acid and one or more 1,1-dihaloethane.

BACKGROUND OF THE INVENTION

Dihaloethanes can be manufactured by using a wide range of processes. Examples of such processes are described in Golubev et al. (Union of Soviet Socialist Republics Inventor Certificate No. 341788). Golubev used hydrofluoric acid to separate 1,1-difluoroethane from vinyl chloride by reacting vinyl chloride with hydrofluoric acid, and then distilling 1,1-difluoroethane. Guofei et al. (Chinese Patent Application Publication No. 1069019a) use both a water scrubber and caustic scrubber to remove acid from a 1,1-difluoroethane product stream. There is no disclosure of separating the dihaloethanes from each other.

Tatsuya et al. (Japanese Patent Publication Kokoku JP-48-16487) describe a method for purifying 1-chloro-1-fluoroethane by absorbing and dissolving the absorbed material in a chlorinated hydrocarbon.

Mao et al (Canadian Patent Application Publication No. 1,074,434 A) use a photochlorination reaction to purify 1,1-difluoroethane.

Brock et al. (U.S. Pat. No. 3,190,930) discloses a process for producing 1-1-difluoroethane from acetylene.

The disclosure of the above-identified documents is hereby incorporated by reference.

SUMMARY OF THE INVENTION

Difluoroethane ($CHF_2CH_3$ or HFC-152a) may be used either alone or in blends with other fluorocarbons as a refrigerant, blowing agent, propellant, an aerosol, as an intermediate product in the manufacture of other fluorinated compounds including vinyl fluoride, among other applications. Hydrofluorocarbons (HFCs) such as 1,1-difluoroethane are environmentally acceptable replacements for certain chlorofluorocarbons (CFCs) and hydrocarbons.

A difluoroethane containing mixture can be made by any suitable method such as by reacting chloroethene ($CH_2=CHCl$ or vinyl chloride) with hydrofluoric acid, e.g., a method described in the aforementioned U.S. and non-U.S. Patents. Intermediates or by-products to this reaction may include 1-chloro-1-fluoroethane ($CHClFCH_3$ or HCFC-151a) and 1,1-dichloroethane ($CHCl_2CH_3$ or HCC-150a). HCFC-151a and HCC-150a are also potential intermediate products in the manufacture of other fluorocarbon compounds, e.g., vinyl fluoride.

One aspect of the present invention relates to the discovery of azeotropic or azeotrope-like compositions containing effective amounts of hydrofluoric acid with at least one of 1,1-dichloroethane, 1-chloro-1-fluoroethane and 1,1-difluoroethane.

The aforementioned azeotropic or azeotrope-like compositions can be employed in another aspect of the invention which relates to a process for separating HF from first mixture comprising HF and at least one compound selected from the group of 1,1-dichloroethane, 1-chloro-1-fluoroethane, and 1,1-difluoroethane. This process broadly comprises (1) distilling the first mixture to substantially remove all materials that have either (a) a lower boiling point than the lowest boiling azeotrope composition containing HF and said at least one compound or (b) a higher boiling point than the highest boiling azeotrope composition containing HF and said at least one compound thereby forming a second mixture; and (2) distilling the second mixture to recover HF as an azeotropic or azeotrope-like composition containing HF and said at least one compound. This aspect of the instant invention solves problems associated with conventional practices by providing an expedient process for obtaining purified HFC-152a.

If desired the HF can be recovered or separated from the azeotropic or azeotrope-like composition, e.g., by decantation. Depending upon the composition of the dihaloethane component of the azeotrope, the dihaloethane can be recovered as a useful product or employed as a precursor of another fluorocarbon.

DETAILED DESCRIPTION

Figure 1:
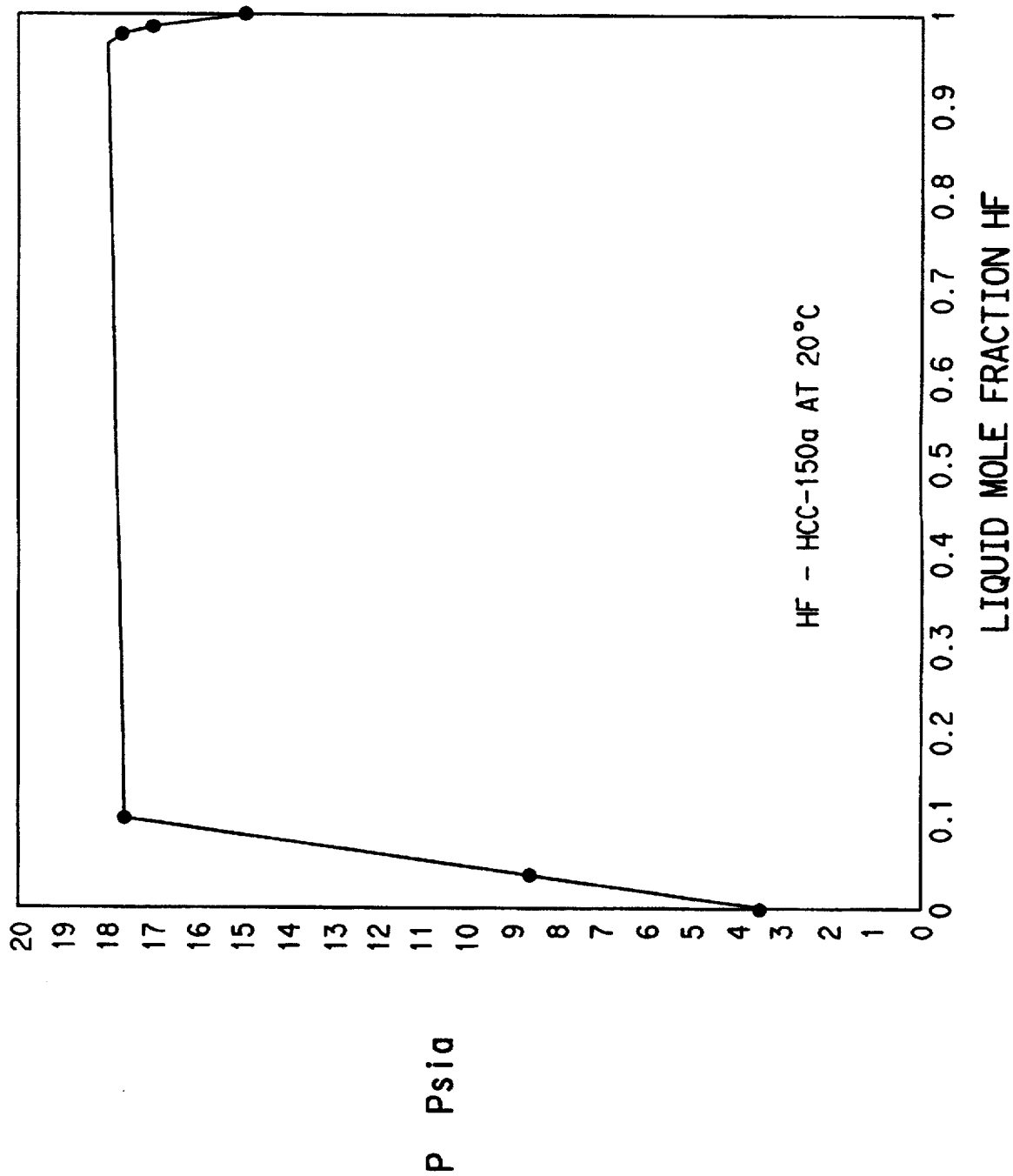
FIG. 1—FIG. 1 is a graphical representation of an azeotropic and azeotrope-like compositions consisting essentially of HF and HCC-150a at a temperature of about 20° C.

The present invention relates to the discovery of azeotropic or azeotrope-like compositions containing effective amounts of hydrofluoric acid with at least one of 1,1-dichloroethane, 1-chloro-1-fluoroethane and 1,1-difluoroethane. This invention also describes a process for separating HF from a mixture comprising HF and at least one of 1,1-dichloroethane, 1-chloro-1-fluoroethane, 1,1-dichloroethane, among others.

By "azeotropic" or an "azeotrope" composition it is meant a constant boiling mixture of two or more substances that behaves as a single substance. One way to characterize an azeotropic composition is that the vapor produced by partial evaporation or distillation of the liquid has the same composition as the liquid from which is was evaporated or distilled; i.e. the mixture distills/refluxes without compositional change. Constant boiling compositions are characterized as azeotropic because they exhibit either a maximum or minimum boiling point, as compared with that of the non-azeotropic mixture of the same components. Azeotropic compositions are also characterized by a minimum or a maximum in the vapor pressure measurements relative to the vapor pressure of the neat components in a PTx cell as a function of composition at a constant temperature.

By "azeotrope-like" is meant a composition that has a constant boiling characteristic or a tendency not to fractionate upon boiling or evaporation. Therefore, the composition of the vapor formed is the same as or substantially the same as the original liquid composition. During boiling or evaporation, the liquid composition, if it changes at all, changes only to a minimal or negligible extent. An azeotrope-like composition can also be characterized by the area that is adjacent to the maximum or minimum vapor pressure. This can be seen by plotting vapor pressure at a given temperature as a function of mole fraction.

It is recognized in the art that a composition is azeotrope-like if, after about 50 weight percent of the composition is removed such as by evaporation or boiling off, the difference between the original composition and the composition remaining is less than about 6% and normally less than about 3% relative to the original composition.

By "effective amount" it is meant an amount of at least one dihaloethane which, when combined with HF, results in the formation of an azeotrope or azeotrope-like composition. This definition includes the amounts of each component, which amounts may vary depending on the pressure applied to the composition so long as the azeotropic or azeotrope-like compositions continue to exist at the different pressures, but with possible different boiling point temperatures. Effective amount also includes the amounts, such as may be expressed in weight percentages or mole percentages, of each component of the compositions of the instant invention which form azeotropic or azeotrope-like compositions at temperatures or pressures other than as described herein. Therefore, included in this invention are compositions of effective amounts of HCC-150a and HF, HCFC-151a and HF, and HFC-152a and HF such that after about 50 weight percent of an original composition is evaporated or boiled off to produce the remaining composition, the difference between the original composition and the remaining composition is typically about 6 percent or less and normally 3 percent or less.

It is also possible to characterize an azeotropic or azeotrope-like compositions as a substantially constant boiling admixture which may appear under many guises, depending upon the conditions chosen, by several criteria:

The composition can be defined as an azeotrope of HF ("A") and HFC-152a ("B"), or of HF ("A") and HCC-150a ("C"), or of HF ("A") and HCFC-151a ("D"), among others, because the term "azeotrope" is at once both definitive and limitative, and requires effective amounts of A and B, or A and C, or A and D for this unique composition of matter which can be a constant boiling composition.

It is well known by those skilled in the art, that, at different pressures, the composition of a given azeotrope will vary at least to a degree, and changes in pressure will also change, at least to some degree, the boiling point temperature. Thus, an azeotropic or azeotrope-like composition of HF ("A") and HFC-152a ("B"), or of HF ("A") and HCC-150a ("C"), or of HF ("A") and HCFC-151a ("D"), among others, represents a unique type of relationship but with a variable composition which depends on temperature and/or pressure. Therefore, compositional ranges, rather than fixed compositions, are often used to define azeotropes.

The composition can be defined as a particular weight percent relationship or mole percent relationship of HF ("A") and HFC-152a ("B"), or of HF ("A") and HCC-150a ("C"), or of HF ("A") and HCFC-151a ("D"), among others, while recognizing that such specific values point out only one particular relationship and that in actuality, a series of such relationships, presented by A and B, or A and C, or A and D, actually exist for a given azeotrope, varied by the influence of pressure.

An azeotrope or azeotrope-like composition of HF ("A") and HFC-152a ("B"), or of HF ("A") and HCC-150a ("C"), or of HF ("A") and HCFC-151a ("D"), among others, can be characterized by defining the compositions as an azeotrope characterized by a boiling point at a given pressure, thus given identifying characteristics without unduly limiting the scope of the invention by a specific numerical composition, which is limited by and is only as accurate as the analytical equipment available.

It is recognized in the art that both the boiling point and the weight (or mole) percentages of each component of the azeotropic composition may change when the azeotrope or azeotrope-like liquid composition is subjected to boiling at different pressures. Thus, an azeotrope or an azeotrope-like composition may be defined in terms of the unique relationship that exists among components or in terms of the compositional ranges of the components or in terms of the exact weight (or mole) percentages of each component of the composition characterized by a fixed boiling point at a specific pressure.

It is also recognized in the art that when the relative volatility of a system, e.g., HF and at least one dihaloethane, approaches 1.0 such defines the system as forming an azeotrope-like composition. When the relative volatility is 1.0 such defines the system as forming an azeotrope.

To determine relative volatility of HF opposite each of HCC-150a, HCFC-151a, and HFC-152a, the so called PTx method was used. In this procedure, the total absolute pressure in a PTx cell of known volume is measured at a constant temperature for various known binary compositions. Use of the PTx method is described in greater detail in Phase Equilibrium in Process Design Wiley-Interscience Publisher, 1970, written by Harold R. Null, on pages 124 to 126, the entire disclosure of which is hereby incorporated by reference.

These PTx measurements can be reduced to equilibrium vapor and liquid compositions in the cell by an activity coefficient equation model, such as the Non-random, Two Liquid (NRTL) equation, to represent liquid phase non-idealities. Use of an activity coefficient equation, such as the NRTL equation, is described in greater detail in Phase Equilibria in Chemical Engineering, published by Butterworth Publishers, 1985, written by Stanley M. Walas, pages 165 to 244; the entire disclosure is hereby incorporated by reference.

The behavior of hydrogen fluoride may also be calculated by using an appropriate hydrogen fluoride association model in conjunction with the aforementioned methods as described by W. Schotte, Ind. Eng. Chem. Process Des. Dev. 1980, 19, pp 432–439; the entire disclosure of which is hereby incorporated by reference.

Without wishing to be bound by any theory or explanation, it is believed that the NRTL equation can sufficiently predict whether or not mixtures of HF and any of the dihaloethanes behave in an ideal manner, and can sufficiently predict the relative volatilities of the components in such mixtures.

Thus, while HFC-152a has a good relative volatility compared to HF at low HFC-152a concentrations, the relative volatility becomes nearly 1.0 as about 91.5 mole percent HFC-152a is approached at a temperature of about 95° C. A relative volatility of 1.0 would make it virtually impossible to effectively separate HFC-152a from HF by conventional distillation from such a mixture.

Referring now to FIG. 1. FIG. 1 illustrates graphically the formation of an azeotropic and azeotrope-like composition consisting essentially of HF and HCC-150a at a temperature of about 20° C. This azeotropic or azeotrope-like composition has a higher vapor pressure than either pure component, with the composition of the vapor space in the maximum pressure region being that of the azeotrope. This system exhibits a maximum at about 92.5 mole percent (or 71.4 weight %) HF at a temperature of about 20° C. and about 18 psia. By sampling the vapor space in the PTx cell and employing NRTL calculations also show that the azeotropic or azeotrope-like compositions exhibit a maximum at about 94 mole percent (77.3 weight %) HF at a temperature of about 0° C. at 8 psia. Based on these findings, it has been calculated that an azeotropic or azeotrope-like composition of about 86.1 mole percent (55.6 weight %) HF is formed at a temperature of about 70° C. and 90.1 psia. Accordingly, the present invention provides an azeotropic or azeotrope-like composition consisting essentially from about 86 to 95 mole % HF and 14 to 5 mole % HCC-150a, said composition having a boiling point from about 0° C. at 8 psia to about 70° C. at 90 psia.

Figure 2:
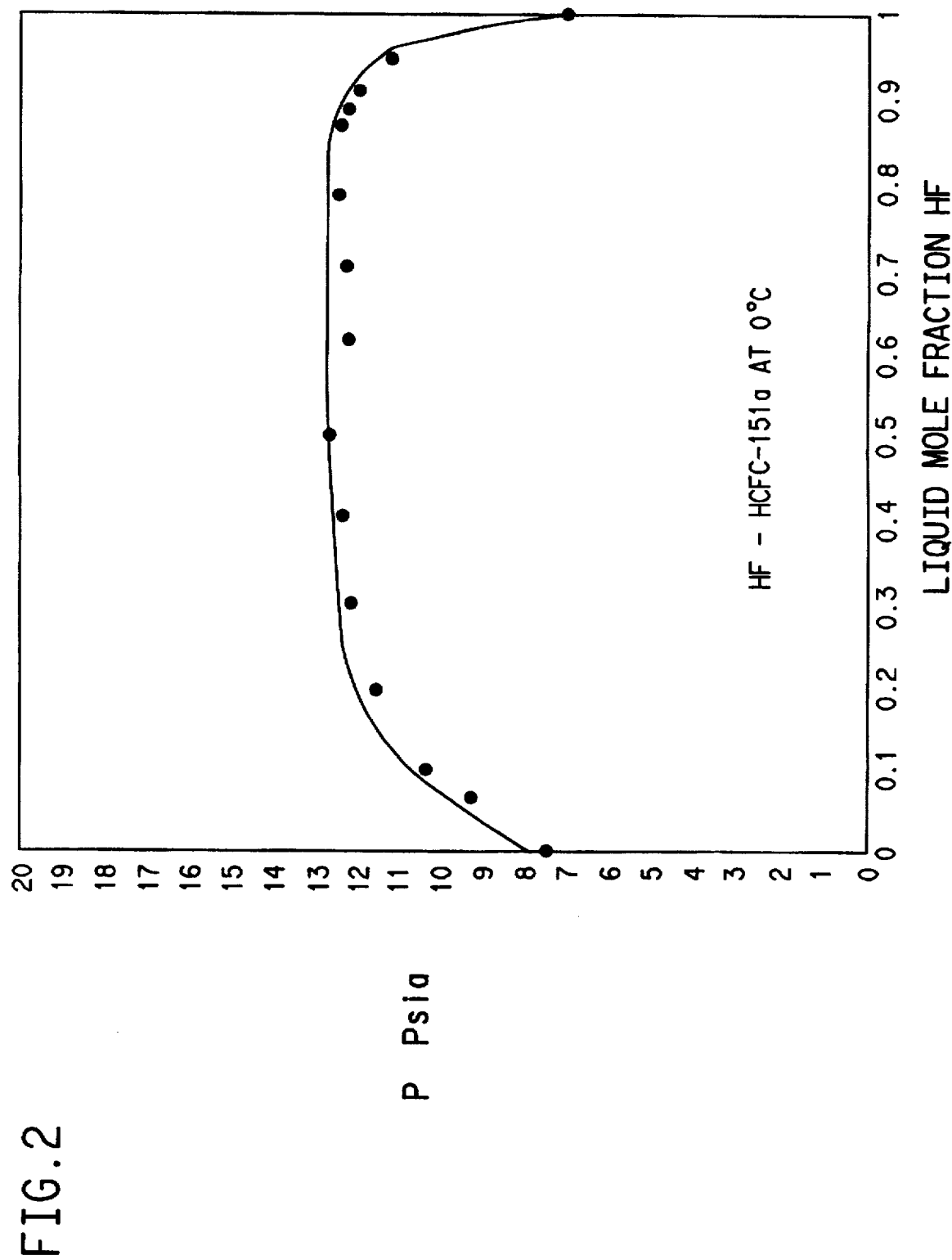
FIG. 2—FIG. 2 is a graphical representation of an azeotropic and azeotrope-like compositions consisting essentially of HF and HCFC-151a at a temperature of about 0° C.

Referring now to FIG. 2, FIG. 2 illustrates the formation of an azeotropic or azeotrope-like composition consisting essentially of HF and HCFC-151a. This composition exhibits a maximum vapor pressure at about 71.6 mole percent (37.9 weight %) HF at a temperature of about 0° C. and a pressure of about 12.8 psia. An azeotropic or azeotrope-like composition also formed at about 59.8 mole percent (26.5 weight %) HF at 80° C. and a pressure of about 160 psia. Accordingly, the present invention provides an azeotropic or azeotrope-like composition consisting essentially from about 71 to 60 mole % HF and 29 to 40 mole % HCFC-151a, said composition having a boiling point from about 0° C. at 13 psia to about 80° C. at 160 psia.

Figure 3:
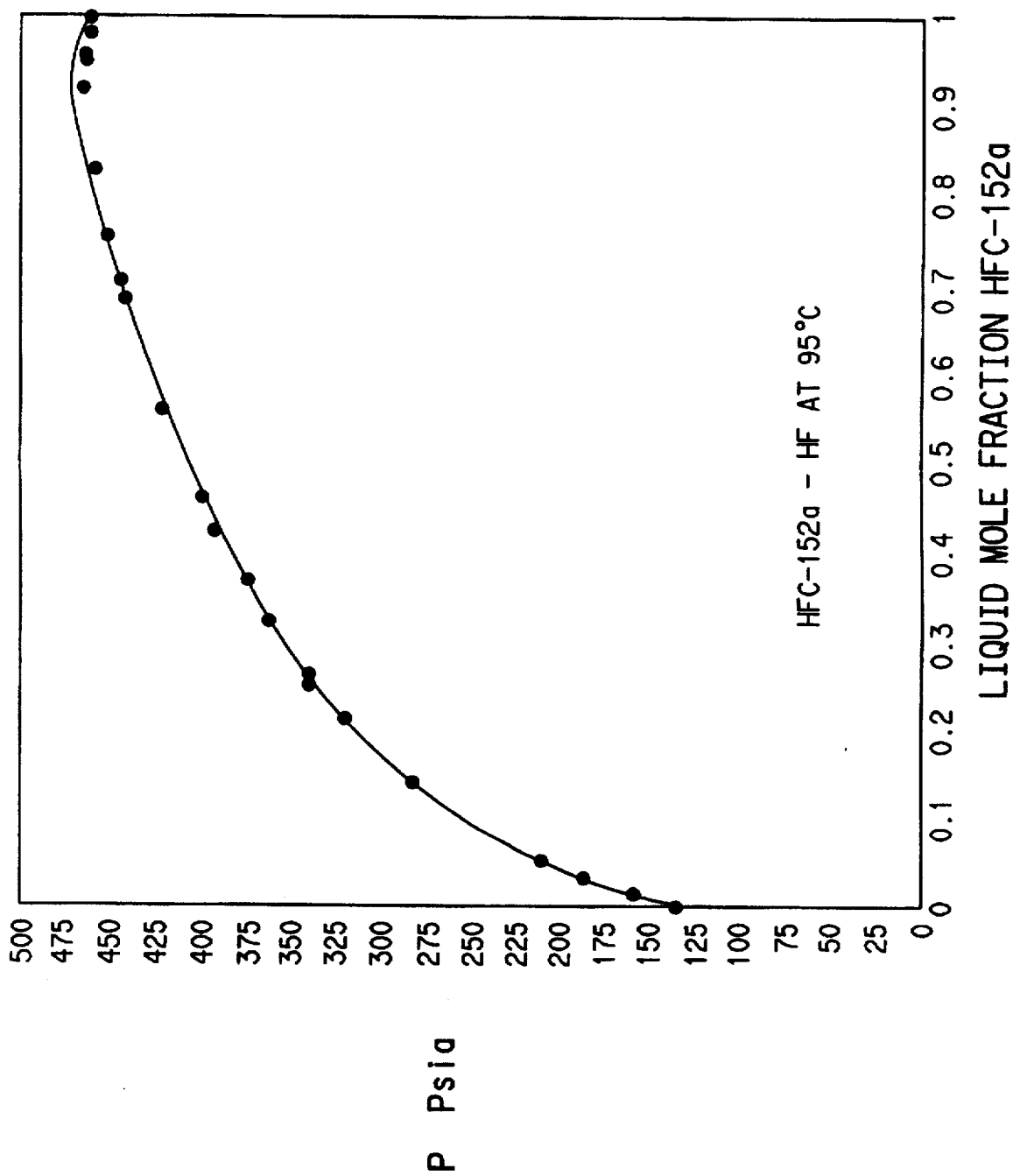
FIG. 3—FIG. 3 is a graphical representation of an azeotropic and azeotrope-like compositions consisting essentially of HF and HFC-152a at a temperature of about 95° C.
Figure 4:
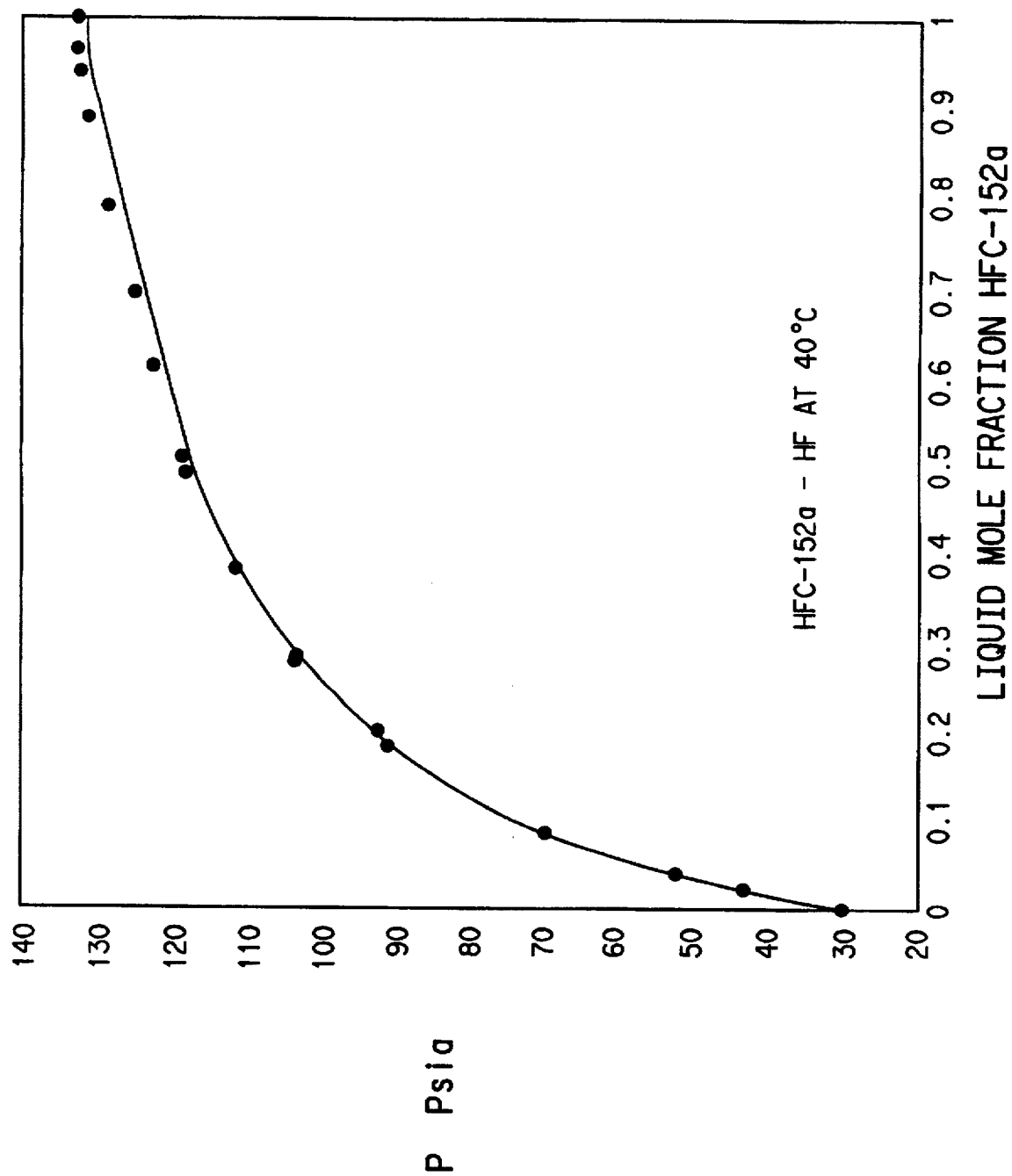
FIG. 4—FIG. 4 is a graphical representation of an azeotropic and azeotrope-like compositions consisting essentially of HF and HFC-152a at a temperature of about 40° C.

Referring now to FIG. 3, FIG. 3 illustrates the formation of an azeotropic or azeotrope-like composition consisting essentially of HF and HFC-152a. This composition exhibits a maximum at 8.45 mole percent (2.7 weight %) HF at a temperature of about 95° C. at about 464 psia. While no azeotrope was evident at about 0° C., an azeotropic and azeotrope-like compositions were indicated at a temperature of about 40° C. Referring now to FIG. 4, FIG. 4 illustrates the vapor pressure for a composition consisting essentially of HF and HFC-152a at a temperature of about 40° C. Based on this data, NRTL calculations show that an azeotropic or azeotrope-like composition of about 1.0 mole % (0.3 weight %) HF is formed at about 45° C. and 150 psia. Accordingly, the present invention provides an azeotropic or azeotrope-like composition consisting essentially of less than about 9 mole % HF and more than 91 mole % HFC-152a, said composition having a boiling point from about 45° C. at 150 psia to about 95° C. at 464 psia.

In one aspect, the instant invention relates to a process for separating HF from a first mixture comprising HF, at least one of the 1,1-dihaloethanes, among other substances. The dihaloethanes comprise at least one member selected from the group consisting of 1,1-dichloroethane, 1-chloro-1-fluoroethane, and 1,1-difluoroethane. In accordance with this aspect of the invention, the first mixture is distilled to substantially remove all substances which have a lower boiling point than the lowest boiling azeotropic or azeotrope-like composition containing HF and a 1,1-dihaloethane; thereby forming a second mixture. Such low-boiling materials can include, for example, HCl, low-boiling halogenated hydrocarbons, e.g., vinyl fluoride. The second mixture can be recovered as a useful product, or further processed by using the inventive azeotropic distillation process, e.g., one or more azeotropic compositions are removed from higher boiling substances.

If desired, the lowest boiling azeotropic or azeotrope-like composition containing HF and a dihaloethane is then distilled from the second mixture such that HF is removed from the second mixture as an azeotropic composition containing HF and the dihaloethane. For example, when the second mixture, i.e., the mixture obtained from the first mixture after distilling components boiling at lower temperatures than the lowest boiling azeotrope of HF with a 1,1-dihaloethane, consists essentially of relatively small quantities of HF and HFC-152a, the HF may be separated from the second mixture and recovered as an azeotrope consisting essentially of HFC-152a and HF. By "relatively small quantities" of HF, it is meant that the second mixture contains less than about 2.7 wt % HF. For best results, the HF that is employed in azeotropic distillation is anhydrous. If excess amounts of HFC-152a or HF remain in the second mixture after the azeotropes are removed, such excess may be recovered as a relatively pure compound.

When the second mixture consists essentially of HF and HCFC-151a e.g., substantially free of HFC-152a, HF may be separated from the second mixture and recovered as an azeotropic or azeotrope-like composition consisting essentially of HCFC-151a and HF. If excess amounts of HCFC-151a or HF remain after the azeotropes are recovered, such excess may be recovered as a relatively pure compound.

When the second mixture consists essentially of HF and HCC-150a e.g., substantially free of HFC-152a and HCFC-151a, HF may be separated from the second mixture as an azeotropic or azeotrope-like composition consisting essentially of HCC-150a and HF. If excess amounts of HCC-150a of HF remain after the azeotropes are recovered, such excess may be recovered as a relatively pure compound.

Alternatively, the first mixture is distilled to substantially remove all substances which have a higher boiling point than the highest boiling azeotropic or azeotrope-like composition containing HF and a dihaloethane; thereby forming a second mixture. Such high-boiling materials can include, for example, high boiling halogenated hydrocarbons. The highest boiling mixture containing HF and dihaloethane is then distilled such that HF is separated from the second mixture and recovered as an azeotropic or azeotrope-like composition containing HF and the 1,1-dihaloethane.

In all of the aforementioned aspects of the invention, either the overhead product stream or the tails from the distillation column can be recovered as a useful product, recycled to the distillation column, transported to a reactor containing chloroethene, converted into a fluorocarbon, among other uses.

Figure 5:
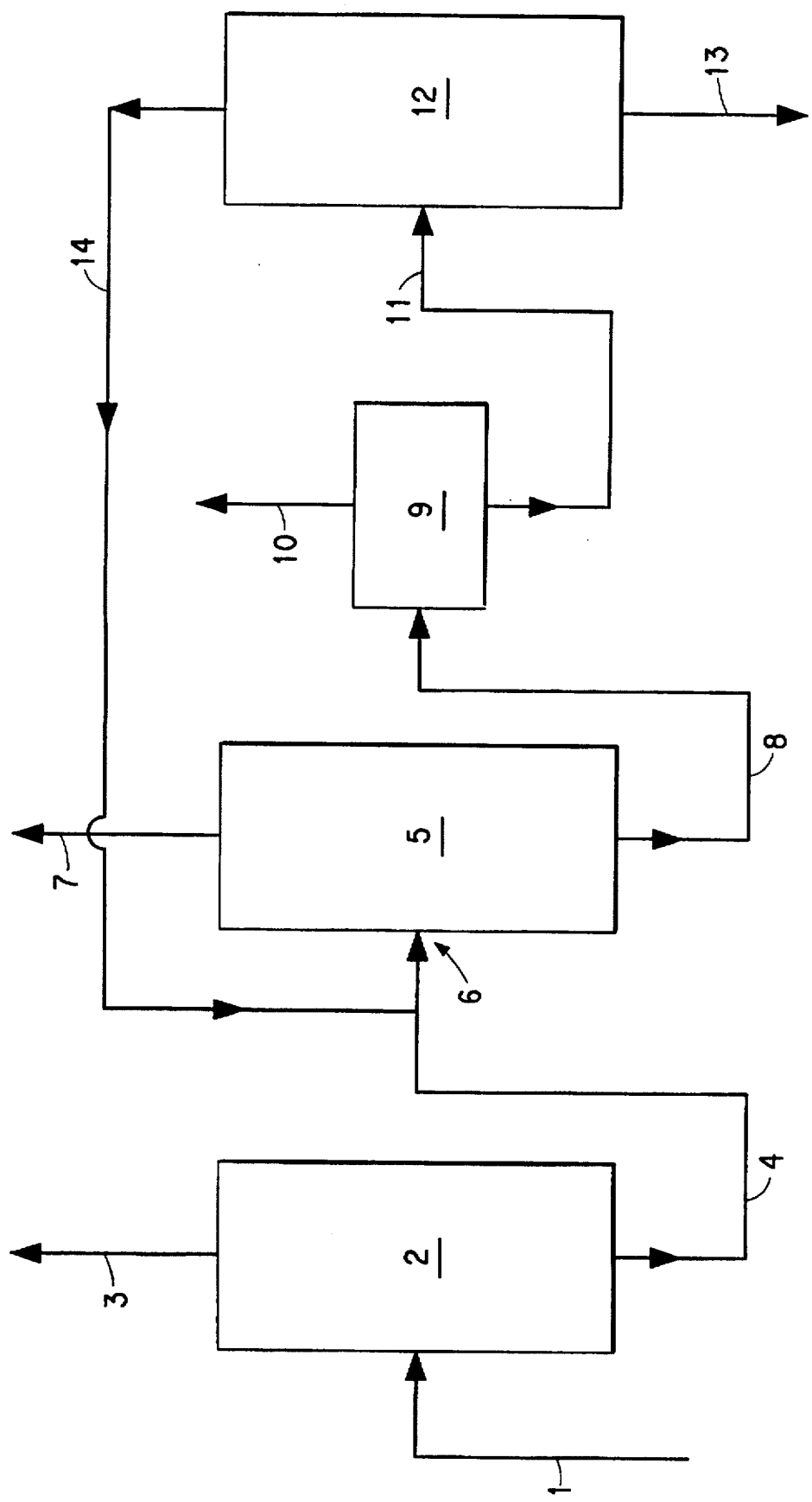
FIG. 5—FIG. 5 is a schematic of one aspect of the invention that employs azeotropic distillation.

Referring now to FIG. 5, FIG. 5 shows a schematic of a process that can also be employed in accordance with the instant invention for separating HF and each of the dihaloethanes from a mixture comprising HF and at least one of the dihaloethanes. The first mixture can be a product stream from an HFC-152a manufacturing process. A first mixture comprising hydrofluoric acid with at least one of HCC-150a, HCFC-151a and HFC-152a is introduced through conduit 1 into a first separation column 2. Column 2 is a distillation column of conventional design that is operated at a pressure between approximately 14.7 and 300 psia. An HFC-152a/HF azeotrope is recovered from conduit 3 as an overhead product and, if desired, can be deacidified with caustic to produce substantially acid-free HFC-152a product. A second mixture is removed from column 2 through conduit 4 and introduced into a second column 5 at feed point 6. Column 5 is a distillation column of conventional design. The second column 5 employs an HF/HCFC-151 azeotrope (a low-boiling azeotrope) to separate HCFC-151a from the mixture within column 5. The HCFC-151a/HF azeotrope or azeotrope-like composition is recovered as an overhead product of column 5 from conduit 7.

In some cases, the second column 5 may also be operated between about 14.7 and 300 psia. A third mixture can be taken from the bottoms of second column 5 and transported via conduit 8 into a decanter 9. The decanter 9 is maintained at a temperature sufficient to convert the third mixture into HF-rich and HCC-150a-rich phases. The HF-rich phase can be removed from the decanter 9 and recycled via conduit 10 into an HFC-152a manufacturing process. The HCC-150a-rich phase can be removed from the decanter 9 and transported via conduit 11 to a third column 12. Column 12 is a distillation column of conventional design.

The third column 12 employs an HCC-150a/HF low-boiling azeotrope and (to a lesser extent) HF/HCFC-151a azeotrope to remove HF from the mixture in conduit 11. The operating pressure for the third column 12 can range between about 14.7 and 300 psia. By employing an operating pressure that is as low as possible (excluding vacuum), the base temperature of column 12 can be minimized. The column 12 tails stream 13 comprises a substantially acid-free HCC-150a product. The overhead product or column distillate stream 14 consists essentially of the HF/HCC-150a and HF/HCFC-151a azeotropes and azeotrope-like compositions and, if desired, may be recycled to the second column 5.

In some cases, the first mixture comprises hydrofluoric acid with HCC-150a and HCFC-151a; but is substantially HFC-152a-free. In this case the first mixture may be fed directly into the second column 5, i.e., omitting the column 2. Should the first mixture comprise hydrofluoric acid, HCC-150a and HFC-152a; but is substantially HFC-151a-free, the second column 5 may be omitted and the mixture in conduit 4 may be introduced directly into decanter 9. Should the first mixture comprise hydrofluoric acid, HCFC-151a and HFC-152a; but is substantially HCC-150a-free, both the decanter 9 and the third column 12 may be omitted. In the later case, the bottoms from second column 5 that are transported via conduit 8 will typically contain HF. Such HF may be recycled to an HFC-152a manufacturing process to increase the yield of HFC-152a.

The distillation of azeotropes containing HF and 1,1-dihaloethanes typically may be practiced on a batch or continuous process and at a wide variety of temperatures and pressures. Operating conditions are determined by temperatures and pressures suitable for azeotropic formation. The inventive azeotropic distillation can be practicing by employing distillation equipment having known structure.

The distillation equipment and its associated feed lines, effluent lines and associated units should be constructed of materials resistant to HF and HCl. Typical materials of construction, well-known to the fluorination art, include stainless steels and the well-known high nickel alloys, such as Monel® nickel-copper alloys, Hastelloy® nickel-based alloys and, Inconel® nickel-chromium alloys.

While the above description placed particular emphasis upon using azeotrope distillation for separating HF from the second mixture, the azeotropic distillation can be practiced at any expedient location. Further, azeotropic distillation can be practiced before or after a conventional distillation process depending upon the relative quantities of substances in the first mixture and the composition of the desired final product. Although the first mixture will typically contain relatively large quantities of dihaloethane, it is to be understood that the instant invention can be practiced upon a virtually unlimited array of mixtures that comprise but not limited to HF and at least one dihaloethane.

Specific examples illustrating the invention are given below. It is to be understood that these examples are merely illustrative and in no way are to be interpreted as limiting the scope of the invention.

EXAMPLE 1

A phase study was performed for a composition consisting essentially of HCC-150a and HF wherein the composition was varied and the vapor pressures were measured at the given temperatures:

| Mole % of HF in | | Pressure | Relative Volatility | Temp. |
|---|---|---|---|---|
| Liquid | Vapor | (psia) | HCC-150a/HF | (deg. C.) |
| 0.00 | 0.00 | 1.37 | 0.0088 | 0 |
| 2.67 | 77.35 | 4.07 | 0.0117 | 0 |
| 5.83 | 94.49 | 7.91 | 0.0159 | 0 |
| 98.71 | 95.35 | 7.91 | 9.6 | 0 |
| 100.00 | 100.00 | 6.99 | 13.0 | 0 |
| 0.00 | 0.00 | 3.57 | 0.0151 | 20 |
| 3.05 | 62.62 | 8.67 | 0.0193 | 20 |
| 5.97 | 84.13 | 12.34 | 0.0240 | 20 |
| 10.14 | 93.01 | 17.62 | 0.0318 | 20 |
| 98.00 | 93.12 | 17.62 | 9.20 | 20 |
| 98.98 | 95.62 | 16.93 | 11.31 | 20 |
| 100.00 | 100.00 | 15.05 | 14.23 | 20 |

The components of the composition were only partially miscible and form several liquid phases. The composition listed above is of the bulk liquid phase.

This composition exhibits a maximum vapor pressure at about 92.5 mole percent HF at a temperature of about 20° C., e.g., refer to FIG. 1, and a maximum vapor pressure at about 94 mole percent HF at a temperature of about 0° C. whereat the vapor composition at these maxima correspond to the respective azeotropic composition (at the given temperature).

EXAMPLE 2

A phase study was performed for a composition consisting essentially of HF and HCFC-151a wherein the composition was varied and the vapor pressures were measured at the given temperatures:

| Mole % of HF in | | Pressure | Relative Volatility | Temp. |
|---|---|---|---|---|
| Liquid | Vapor | (psia) | HCC-151a/HF | (°C.) |
| 0.00 | 0.00 | 7.59 | 0.150 | 0 |
| 5.37 | 26.97 | 9.48 | 0.160 | 0 |
| 9.93 | 47.42 | 10.41 | 0.127 | 0 |
| 19.79 | 65.81 | 11.57 | 0.134 | 0 |
| 30.12 | 69.99 | 12.18 | 0.193 | 0 |
| 40.10 | 71.48 | 12.48 | 0.280 | 0 |
| 50.10 | 72.37 | 12.75 | 0.401 | 0 |
| 61.62 | 72.78 | 12.30 | 0.629 | 0 |
| 69.90 | 72.61 | 12.36 | 0.917 | 0 |

-continued

| Mole % of HF in | | Pressure | Relative Volatility | Temp. |
|---|---|---|---|---|
| Liquid | Vapor | (psia) | HCC-151a/HF | (°C.) |
| 77.00 | 72.35 | 12.50 | 1.3402 | 0 |
| 87.00 | 73.33 | 12.39 | 2.5551 | 0 |
| 88.24 | 73.79 | 12.28 | 2.7957 | 0 |
| 91.05 | 75.54 | 12.04 | 3.4564 | 0 |
| 94.95 | 80.72 | 11.18 | 4.7188 | 0 |
| 100.00 | 100.00 | 6.99 | 7.1772 | 0 |

This composition exhibits a maximum vapor pressure at 71.6 mole percent HF at a temperature of about 0° C.

EXAMPLE 3

A phase study was performed for a composition consisting essentially of HF and HFC-152a wherein the composition was varied and the vapor pressures were measured at the given temperatures:

| Mole % of HF in | | Pressure | Relative Volatility | Temp. |
|---|---|---|---|---|
| Liquid | Vapor | (psia) | HCC-152a/HF | (°C.) |
| 0.00 | 0.00 | 17.42 | 1.44 | −20 |
| 5.07 | 3.21 | 17.31 | 1.61 | −20 |
| 20.73 | 11.60 | 16.80 | 1.99 | −20 |
| 39.20 | 17.01 | 16.33 | 3.15 | −20 |
| 51.21 | 20.30 | 15.96 | 4.12 | −20 |
| 61.21 | 23.50 | 15.46 | 5.14 | −20 |
| 71.39 | 27.70 | 14.77 | 6.51 | −20 |
| 81.38 | 34.26 | 13.49 | 8.39 | −20 |
| 95.46 | 63.53 | 7.58 | 12.07 | −20 |
| 100.00 | 100.00 | 2.82 | 13.35 | −20 |
| 0.00 | 0.00 | 133.00 | 0.979 | 40 |
| 2.70 | 2.45 | 132.60 | 1.10 | 40 |
| 5.12 | 4.23 | 132.30 | 1.22 | 40 |
| 10.90 | 7.47 | 131.60 | 1.51 | 40 |
| 21.04 | 11.87 | 128.60 | 1.98 | 40 |
| 30.16 | 15.27 | 125.50 | 2.40 | 40 |
| 39.71 | 18.48 | 122.20 | 2.91 | 40 |
| 51.32 | 22.34 | 117.00 | 3.67 | 40 |
| 61.53 | 26.30 | 111.60 | 4.48 | 40 |
| 71.93 | 31.92 | 104.10 | 5.47 | 40 |
| 82.09 | 41.27 | 91.40 | 6.52 | 40 |
| 95.86 | 75.12 | 52.40 | 7.67 | 40 |
| 100.00 | 100.00 | 29.80 | 7.76 | 40 |
| 0.00 | 0.00 | 461.20 | 0.774 | 95 |
| 1.23 | 1.48 | 461.81 | 0.827 | 95 |
| 5.09 | 5.47 | 463.85 | 0.927 | 95 |
| 5.38 | 5.73 | 464.15 | 0.935 | 95 |
| 8.34 | 8.20 | 464.04 | 1.02 | 95 |
| 8.45 | 8.29 | 464.39 | 1.02 | 95 |
| 16.85 | 13.66 | 459.82 | 1.28 | 95 |
| 25.31 | 17.77 | 450.11 | 1.57 | 95 |
| 31.91 | 20.57 | 439.86 | 1.81 | 95 |
| 44.54 | 25.61 | 418.46 | 2.33 | 95 |
| 56.95 | 30.94 | 392.14 | 2.95 | 95 |
| 67.74 | 36.93 | 361.50 | 3.59 | 95 |
| 74.69 | 42.30 | 335.67 | 4.03 | 95 |
| 84.28 | 53.77 | 282.26 | 4.61 | 95 |
| 95.86 | 82.17 | 184.82 | 5.03 | 95 |
| 100.00 | 100.00 | 134.35 | 5.01 | 95 |

This composition exhibits a maximum vapor pressure at 8.45 mole % HF at a temperature of about 95° C. As the temperature decreases the composition still exhibits an azeotropic or azeotrope-like behavior as indicated by there continuing to be a maximum vapor pressure for mixtures of these compositions compared to the pure components; but the azeotrope contains less HF as the temperature is lowered. Using the above data, NRTL calculations show that an azeotropic or azeotrope-like composition of about 1.0 mole % HF and 99.0 mole % is formed at a temperature of about 45° C. and about 150 psia. Below about 40° C., the maximum pressure of the system is essentially that of pure HFC-152a thereby indicating the absence of an azeotrope between HF and HFC-152.

The change in the azeotropic or azeotrope-like composition as a function of temperature may be used for separating mixtures of HF and HFC-152a. For example, temperature and pressure can be employed to manipulate the composition of an azeotrope that is recovered.

In the following Examples 4–7, each stage of the distillation column is operated at 100% efficiency.

EXAMPLE 4

In this example, the system of apparatus illustrated in FIG. 5 is employed. The liquid feed to the first column comprises approximately 20.86% by weight HF, 20.63% HCC-150a, 17.20% HCFC-151a, and 41.31% HFC-152a. The first column has 42 stages, and the liquid feed enters the column at stage 18. The first column is operated approximately at a pressure of 64.7 psia, a base temperature of 50° C. and the reflux ratio is 5:1.

The second column has 32 stages. The feed enters the second column at stage 16. The base temperature of the second column is maintained at about 50° C. The operating pressure is about 54.7 psia with a reflux ratio of about 5:1. The third column has 32 stages with the feed entering at stage 16. The third column is operated at a pressure of about 19.7 psia with a reflux ratio of about 3:1.

The compositions of the feeds material, and the streams leaving both the tops and the bottoms of the distillation columns are given below. The number in parenthesis following the stream corresponds to the reference number shown in FIG. 5. The flow rate is in pounds/hour:

| stream | HCC-150a | HCFC-151a | HFC-152a | HF |
|---|---|---|---|---|
| feed mixture (1) | 989.6 | 825.1 | 1981.6 | 1000.4 |
| FIRST COLUMN | | | | |
| Top (3) | — | 0.4 | 1981.6 | 21.6 |
| Bottom (4) | 989.6 | 824.7 | — | 978.8 |
| SECOND COLUMN | | | | |
| Feed (6) | 1024.5 | 832.0 | — | 985.6 |
| Top (7) | — | 823.6 | — | 376.4 |
| Bottom (8) | 1024.5 | 8.3 | — | 609.2 |
| DECANTER | | | | |
| HF-rich phase (11) | 36.9 | 1.0 | — | 6.8 |
| HCC-150a-rich phase (10) | 987.5 | 7.3 | — | 602.4 |
| THIRD COLUMN | | | | |
| Top (14) | 34.9 | 7.3 | — | 6.8 |
| Bottom (13) | 952.7 | — | — | — |

This Example illustrates employing all three of the HF/dihaloethane azeotropic or azeotrope-like compositions. The first distillation column employs an HFC-152a/HF azeotrope to separate relatively high purity HFC-152a from the first mixture, e.g., about 99.98 weight % pure HFC-152a is obtained after acid scrubbing. The second distillation column employs an HF/HCFC-151a azeotrope to separate HCFC-151a from the second mixture. The amount of HFC-152a and HCC-150a remaining associated with the HCFC-151a is less than about 5 parts per million. The third distillation column employs an HCC-150a/HF low boiling azeotrope, and (to a lesser extent) the HF/HCFC-151a azeotrope to remove excess HF from the HCC-150a product thereby producing HCC-150a having about 99.99 wt % purity.

EXAMPLE 5

Figure 6:
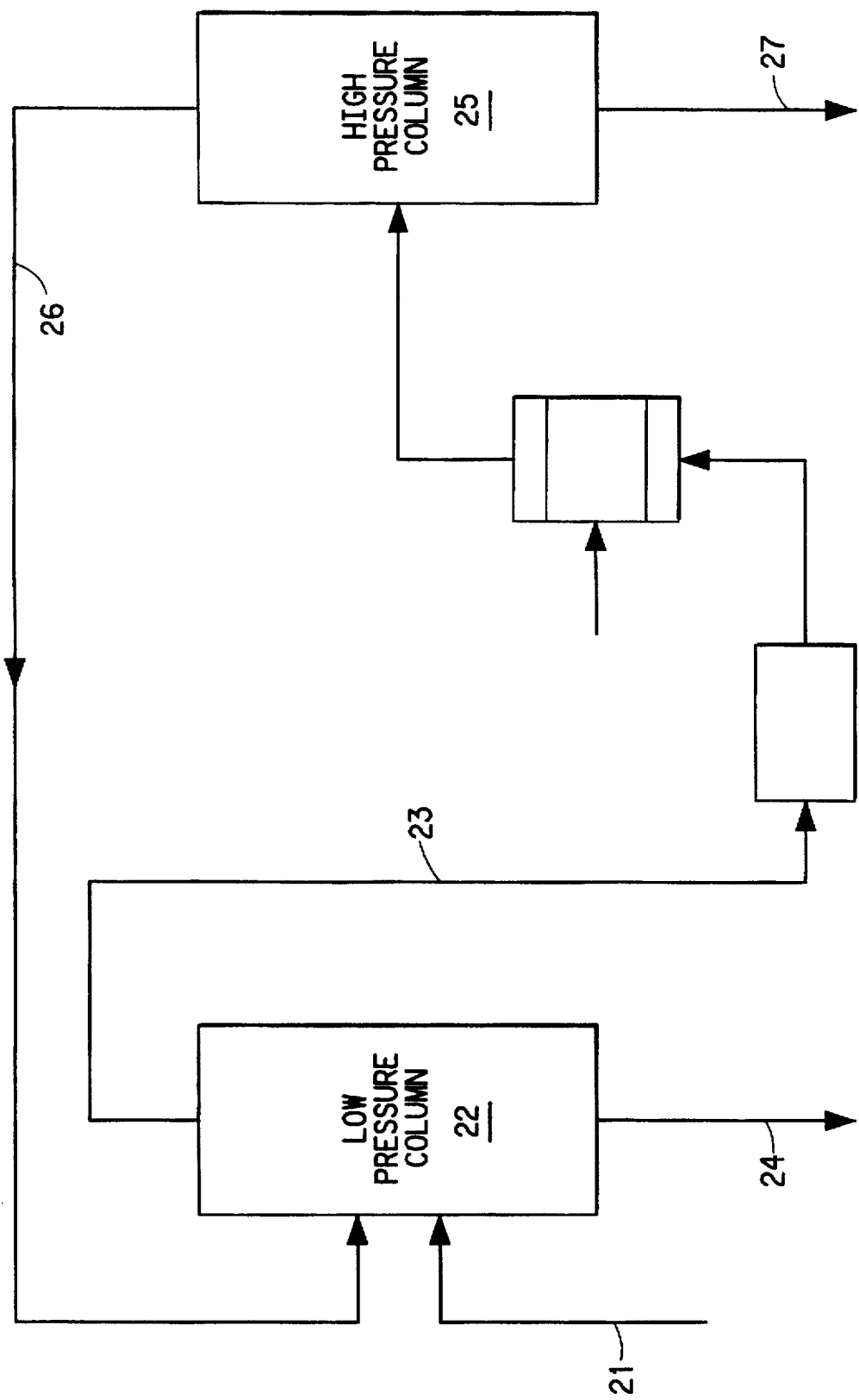
FIG. 6—FIG. 6 is a schematic of another aspect of the invention that employs azeotropic distillation.

This Example demonstrates using pressure-swing distillation, wherein changing the operating temperature/pressure of a distillation may be used for separating HF and HFC-152a. In this Example, the system of apparatus shown in FIG. 6 is employed. The underlined numbers in this Example correspond to the reference numerals shown in FIG. 6.

The first distillation column 22 in this example is the same as the 152a distillation column (the first distillation column described in Example 4) that is illustrated by FIG. 5; but the column 22 is operated at 19.7 psia with a base temperature of 16 deg C. and a condenser temperature of −17 deg c. When the condenser is defined as stage 1, the column has 62 stages wherein the fresh feed stream is fed via line 21 to the column 22 onto stage 31 and the recycle 152a/HF is fed via line 26 onto stage 21. The reflux ratio is 5:1, and the distillate rate is controlled to give 99.99% 151a recovery in the column tails stream exiting via line 24.

The distillate coming overhead via line 23 consists essentially of 2869 pph HFC-152a containing 21 pph HF. This stream's pressure is then increased via a pump and passed through a steam heater. The pressurized stream 23 is fed to a second distillation column 25 operating at 465 psia, with a reboiler temperature of 95 deg C. and a condenser temperature of 94 deg C. When the condenser is defined as stage 1, the column has 82 stages wherein the HF/152a feed mixture X is fed onto stage 31. The reflux ratio is 15:1. Increasing the operating pressure and temperature of the second distillation column 25 in comparison to the overhead stream 23 from the first column 22 causes an azeotrope to form of different composition than the overhead stream from the first column 22. Because the second column L feed contains excess HFC-152a relative to the composition of the azeotrope formed in column 25, HFC-152a free of HF exits from the second column 25 via its bottoms 27. The overhead stream from the second column 25 via line 26, containing the newly formed HF/152a azeotrope, is then recycled back to the first column 22, allowing recovery of any residual HF.

The compositions of the feeds, and the streams leaving both the tops and the bottoms of the distillation columns are given below. The number in parenthesis following the stream corresponds to the reference number shown in FIG. 6. The flow rate is in pounds/hour:

| Stream: | Pounds Per Hour Flow | | | |
|---|---|---|---|---|
| | HCC-150a | HCFC-151a | HFC-152a | HF |
| Fresh Feed Mixture (21) | 989.6 | 825.1 | 1981.6 | 1000.4 |
| Recycle Feed Mixture (26) | <0.1 | <0.1 | 887.4 | 20.6 |
| First Column | | | | |
| Top (23) | <0.1 | <0.1 | 2868.9 | 20.6 |
| Bottom (24) | 989.6 | 825.0 | <0.1 | 1000.4 |
| Second Column | | | | |
| Top (26) | <0.1 | <0.1 | 887.4 | 20.6 |
| Bottom (27) | <0.1 | <0.1 | 1981.6 | <0.1 |

EXAMPLE 6

This Example shows using an HF/152a azeotropic or azeotrope-like composition to remove HF from an HCFC-151a containing stream. In this Example, the system of apparatus shown in FIG. 6 is employed. The underlined numbers in this Example correspond to the reference numerals shown in FIG. 6.

HFC-152a is added to a HCFC-151a stream containing 0.5 wt % HF on a HCFC-151a/HF basis. The resulting mixture is fed via line 21 to a first distillation column 22 operated at 465 psia with a base temperature of 157 deg C. and a condenser temperature of 94 deg C. When the condenser is defined as stage 1, column 22 has 42 stages, with the feed stream 21 fed to the column 22 on stage 21. The reflux ratio of the column 22 is 10:1. Under these temperature/pressure conditions, HFC-152a is added in sufficient quantities to form an azeotrope with essentially all the HF, such that the HF exits the column overhead via line 23 as the azeotrope, thereby leaving HCFC-151a to exit via line 24 as a bottom stream free of HF, e.g., <0.01 wt % residual HF.

| | Stream Flows in Pounds Per Hour | | |
|---|---|---|---|
| | HF | HCFC-151a | HFC-152a |
| Column Feed Stream (21) | 5.0 | 1000.0 | 200.0 |
| Overhead Stream (23) | 5.0 | <0.1 | 200.0 |
| Bottom Stream (24) | <0.01 | 999.9 | <0.01 |

EXAMPLE 7

This example shows using the HCC-150a/HF and HCFC-151a/HF azeotropic and azeotrope-like compositions to separate HF from each of HCC-150a and HCFC-151a.

The HF-rich phase exiting the decanter (label as 9 is FIG. 5) in Example 4 still contains trace quantities of HCC-150a and HCFC-151a. In this Example, a stream consisting of 602.39 pph HF, 36.95 pph HCC-150a and 0.99 pph HCFC-151a is fed to a first distillation column (either 2 of FIG. 5 or 22 of FIG. 6) operating at 100 psig, with the reboiler operating at 88 deg C., with the condenser operating at 79 deg C. When the condenser is defined as stage 1, the column has 42 stages, with the feed mixture entering on stage 11. The reflux ratio is 11.9:1.

Under these conditions, HF/HCFC-151a and HF/HCC-150a azeotropic and azeotrope-like compositions are sufficient to cause essentially all the HCC-150a and HCFC-151a to be distilled overhead as a component of the HF azeotropes thereby permitting 556 pph HF to exit the column bottoms. The column bottoms contain a total amount of HCC-150a and HCFC-151a of less than <0.01 pph, thus removing the organics from the HF. The recovered HF can be employed in processes where the presence of the organics may be objectionable.

The following is claimed:

1. An azeotropic or azeotrope-like composition consisting essentially of about 86 to 95 mole % hydrofluoric acid and 14 to 5 mole % 1,1-dichloroethane at a temperature of from about 0° C. to about 70° C. and a pressure of from about 8 psia to about 90 psia.

* * * * *